United States Patent [19]

Muhammad et al.

[11] Patent Number: 5,188,836
[45] Date of Patent: Feb. 23, 1993

[54] SUSTAINED RELEASE FORMULATIONS

[75] Inventors: Nouman Muhammad, Long Valley; Wayne Boisvert, Hopatcong; Michael Harris, Hackettstown; Jay Weiss, East Brunswick, all of N.J.

[73] Assignee: Warner-Lambert Company, Morris Plains, N.J.

[21] Appl. No.: 559,221

[22] Filed: Jul. 27, 1990

[51] Int. Cl.⁵ .............................................. A61K 47/00
[52] U.S. Cl. .................................. 424/431; 424/441; 424/472; 424/474
[58] Field of Search ................ 424/439, 441, 472, 473

[56] References Cited

U.S. PATENT DOCUMENTS

| | | | |
|---|---|---|---|
| 3,993,072 | 11/1976 | Zaffaroni | 128/260 |
| 4,459,279 | 7/1984 | Stricher et al. | 424/19 |
| 4,954,350 | 9/1990 | Jones et al. | 424/493 |

Primary Examiner—Thurman K. Page
Assistant Examiner—D. Garbrielle Phelan
Attorney, Agent, or Firm—Richard S. Bullitt

[57] ABSTRACT

Semi-enteric controlled release formulations are comprised of a biological active agent such as an antibiotic that is blended with a water-soluble bulking agent, the mix then coated onto an inert core. The coated active core is further coated with a mixture comprised of an acrylic copolymer, bulking agent and pH dependent food acid. These different coating components possess different solubility characteristics which result in a gradual release of the active in both the stomach and small intestine that provides an increased bioavailability of the active drug.

8 Claims, No Drawings

SUSTAINED RELEASE FORMULATIONS

FIELD OF THE INVENTION

The present invention relates to pharmaceutical preparations and the controlled, sustained release thereof. In particular, the present invention concerns the sustained release of an antibiotic such as doxycycline hyclate over a period of time after oral administration so that the drug is completely absorbed into the patient's system. The pharmaceutical composition comprises a coated, inert sphere or pellet that initially begins a partial breakdown and absorption of the drug in the stomach with complete release and absorption in the small intestine.

BACKGROUND OF THE INVENTION

Many pharmaceutical delivery systems are known in the art which are designed to either delay the release of the drug until the system reaches a particular region of the digestive tract or they are designed to gradually release the drug immediately after oral administration. Enteric formulations are designed to prevent any release of the drug for bioavailability until the delivery system reaches the intestine. These are generally designed for those pharmaceuticals that cause stomach irritation or distress.

Normally, pharmaceuticals that are highly soluble irrespective of the pH of the surrounding environment can be formulated into sustained release delivery systems relatively easily. The delayed release properties can be attained by several methods. On the one hand, the drug can be embedded into a matrix of other excipients which are relatively water insoluble and hence, dissolve slowly so as to release the drug to the digestive system slowly. Another method is to shape the drug and excipients into granules or pellets as an active core which are then coated with a substance that dissolves slowly. Usually, these methods produce a delivery system that dissolves either entirely in the stomach or intestine but not both.

The other drawback with many of these sustained release delivery systems known in the art is the fact that not all of the drug becomes bioavailable during its passage through the digestive tract and it eventually becomes lost and expelled through the feces. Attempts have been made to get around these problems by mixing the drug with an excipient and then either forming a core material comprised of the drug excipient mixture or by coating an inert core such as a non-pareil seed with the drug/excipient mixture followed by a coating of the entire pellet with a thin polymer film.

A major problem in the coating of the core granules by the methods of the prior art is the need to dissolve the coating materials in organic solvents prior to their application. These solvents are not only expensive but dangerous in that they are highly explosive. They also pose health and environmental problems in that most are highly toxic.

U.S. Pat. No. 4,138,475 to McAinish et al discloses a sustained release formulation for propranolol or pharmaceutically acceptable salts thereof whereby the drug is mixed with non-water swellable microcystalline cellulose and formed into spheroids. These are then coated with a heavy film of hydroxypropyl methyl cellulose (HPMC) and or a plasticizer which prevents any release of the drug in the stomach. Needless to say, not all of the drug becomes bioavailable in the small intestine either.

U.S. Pat. No. 4,837,030 to Valorose et al discloses a sustained release delivery system for tetracycline compounds designed to release a minor amount of the drug slowly in the human stomach and then rapidly release the remainder in the small intestine. This is accomplished by mixing the drug with one or more of a number of excipients such as microcrystalline cellulose, polyvinylpyrrolidone (PVP), carboxymethyl cellulose, etc., and a binder such as gelatin which is then either extruded into a spherical pellet or coated about a non-pareil seed. The pharmaceutical core pellet may then be coated with a thin polymer or left bare; in either case it is only 60-90% released in the course of its passage after ninety (90) minutes.

U.S. Pat. No. 4,832,958 to Baudier et al reveals a galenic form of prolonged release verapamil and its salts by mixing the drug with a wetting agent such as fatty acid esters, lecithin, sucrose, mannitol or sorbitol and then spheronizing or granulating the mixture into micro-granules. These are then coated with a microporous membrane comprised of a polymer such as Eudragit ® E30D, (Rohm Pharma GmbH, Weiterstadt, West Germany), HPMC phthalate and other wetting agents, plasticizers and the like. The formulations are designed to withstand adverse environmental conditions during storage such as high temperatures. The formulation is enteric by nature and the drug does not become bioavailable until the system reaches the small intestine.

U.S. Pat. Nos. 4,795,644 and 4,418,183 to Zentner disclose delivery systems for the controlled release of drugs that is not pH-dependent through the modulation of the release of a core drug through a microporous wall coating using charged, insoluble resins that bear an electrostatic charge that is identical to that of the drug. The charged resin is water insoluble and non-diffusible through the microporous wall while the active drug is diffusible and water soluble. The charged resins may be either anionic or cationic in nature, and include polystyrene, epoxy-amine phenolic or methacrylic backbones and release the drug through the microporous wall according to the osmotic pressure, not the pH of the external environment. This allegedly allows for the tailoring of a whole range of release rates according to the type of drug used.

U.S. Pat. No. 4,438,091 to Gruber et al discloses a composition for the delayed release of bromhexine comprised of a mixture of the bronchodialator with an acid such as fumaric or tartaric acid which is compressed into a spherical tablet and coated with lacquers that are insoluble in gastric juices and soluble in intestinal juices. These comprise copolymers of acrylic acid and methacylic acid esters. Whereas the drug is generally insoluble at the higher pH values of the intestine and would be absorbed too quickly at the lower acidic pH conditions of the stomach, the acidic matrix prevents quick dissolution early and yet promotes the drugs bioavailability further downstream in the digestive tract.

European Patent Appln. No. 0,035,780 to Sekigawa et al discloses a process for the preparation of enterosoluble drugs by coating a solid dosage form of the drug with hydroxypropyl methylcellulose phthalate or acidic succinyl and acetyl esters of HPMC. Triethylcitrate is added as a plasticizer which aids in the binding of the coating material to the core pellet. The coating then resists dissolution in the stomach but completely dissolves in the small intestine.

European Patent Appln. No 0,273,005 to Ventouras discloses a water dispersible tablet comprised of an active pharmaceutical core material, a pH dependent disintegrant such as crospovidone (N-vinyl-2-pyrrolidone) or croscarmellose and a water-swellable agent such as guar gum, alginates, dextran and the like. Once contacted by moisture in the human oral cavity, the swellable material absorbs water and becomes gel-like, aiding passage through the oral cavity and throat. Once the delivery system reaches the acidic pH of the stomach, the disintegrant breaks apart immediately, releasing the drug for complete bioavailability.

None of the aforementioned formulations however, are truly semi-enteric formulations whereby the active pharmaceutical is dispersed slowly and continually from the early stages of the digestive tract throughout its passage in the stomach and small intestine so as to become 100% bioavailable. Moreover, none of the prior art references and formulations provide for the gradual and controlled release of an active pharmaceutical whose bioavailability is evenly distributed over time.

It is an object of the present invention to provide a controlled, semi-enteric formulation of an active pharmaceutical that is slowly and continually dissolved and absorbed throughout its passage through both the gastric and intestinal portions of the digestive system. More specifically it is an object of the present invention to provide an antibiotic formulation that is quasi-enteric in nature, i.e., that is partially bioavailable in both the stomach and the small intestine so as to insure 100% bioavailability in both. In particular, it is an object of the present invention to provide a semi-enteric formulation for an antibiotic which becomes bioavailable throughout its passage in the digestive tract.

SUMMARY OF THE INVENTION

Semi-enteric sustained release pharmaceutical compositions provide for the controlled release of a biological active material such as an antibiotic in both the stomach and small intestine for increased bioavailability. The semi-enteric release is made possible by initially mixing the active drug with a water soluble bulking agent. This mixture is uniformly coated about an inert core material such as a non-pareil seed. This is then further coated with a blend of a methacrylic acid copolymer, a water soluble bulking agent and a food grade acid whose solubility is pH dependent.

Since the pH conditions of the stomach and small intestine differ, the coating materials become soluble at different points in the digestive tract. The water soluble bulking agent will begin to break down in the hydrous environment of the stomach resulting in the partial release of some of the active core. The copolymer and the pH dependent food acid do not dissolve until the pharmaceutical composition enters the more basic environment of the small intestine. Hence, a controlled sustained release of the biological active is achieved throughout both the stomach and intestine thereby resulting in increased bioavailability of the drug.

DETAILED DESCRIPTION OF THE INVENTION

The drug delivery system of the present invention utilizes a unique combination of coating materials that result in a controlled, semi-enteric formulation of the drug that releases throughout the digestive system to insure 100% bioavailability of the active agent. The controlled sustained release of the drug is due to different solubility characteristics of the coating materials which dissolve or break down in different parts of the digestive tract resulting in a gradual, partial release of the drug over time.

The drug is initially mixed with a water soluble bulking agent to form an active matrix that is then uniformly coated about an inert, non-pareil sugar seed. This core is then coated with a mixture of materials that ultimately control release of the drug to the system. The major coating constituent is a methacrylic acid copolymer commercially known as Eudragit ® L30D, a film forming polymer in an aqueous solid dispersion made by Rohm Pharma Gmbh, Weiterstadt, West Germany. In the past, Eudragit ® L30D was employed to prepare fully enteric pharmaceutical formulations. Drugs that are coated with this polymer are not released to the system under the pH conditions existing in the stomach but rather are released when the polymer dissolves under the pH conditions of the intestine. In the present invention, the release characteristics of the Eudragit L30D polymer are modified so that a semi-enteric formulation is developed.

In order to modify the dissolution characteristics of Eudragit ® L30D, a water soluble bulking agent such as a sugar alcohol is mixed with the film forming polymer. Suitable sugar alcohols useful in the practice of the present invention include mannitol, sorbitol, lactitol and the like. Mannitol is the preferred bulking agent in that it will dissolve and break down in any hydrous environment, irrespective of the pH. Another constituent of the coating is a pH- dependent acid such as fumaric acid which will only dissolve and break down in environments with a pH of greater than 3.5. Other suitable food grade acids include malic acid, citric acid, tartaric acid, ascorbic acid and mixtures thereof. Fumaric acid has a very low solubility in water and hence its dissolution will only be triggered by the basic conditions existing in the intestine.

The incorporation of the water soluble bulking agent and the pH dependent acid into the Eudragit ® polymer coating allows for a controlled drug release to be attained in pH regions where there is usually no drug release. This is especially useful for those drugs that irritate the stomach since they do permit some release so as to insure 100% bioavailability without releasing all the drug so as to cause gastric distress. As the bulking agent initially dissolves in the hydrous acidic environment of the stomach, small holes appear in the otherwise uniform, intact coating. The pharmaceutical is gradually released through these holes until the delivery system finally reaches the small intestine where the more basic conditions dissolve and break down both the pH dependent food grade acid and the methacrylic acid copolymer coat. With the systems entry into the more basic environment of the gastrointestinal tract i.e., above 3.5, the pH dependent food acid portion will dissolve and more holes or spots will appear in the methacrylic acid copolymer coat releasing more drug to the system at a greater rate for absorption. Finally, after several minutes of exposure of the methacrylic acid coat to the basic environment of the small intestine, the methacrylic acid copolymer coating breaks down altogether releasing all of the remaining active drug to the system for absorption. The polymer portion of the matrix coating starts to dissolve at pH 6.0.

Other excipients are added to the polymer coating in minor amounts in order to stabilize the composition and to help bind the system together. Plasticizers such as triethyl citrate are added in amounts of up to about 1.5% in order to aid in the flowability of the coating mixture so as to insure maximum uniformity and integrity of the coating. An anti-adherent such as kaolin or talc in amounts of up to about 3.0% is also added as an inert aid in the stability of coating process. Binders such as hydroxypropylcellulose in amounts of from about 0.01 to about 4.0 may also be added to hold the various constituents together.

Whereas the delivery system of the present invention could be tailored to provide a semi-enteric carrier for nearly any active pharmaceutical of choice, the system has proven most effective in the delivery of antibiotics such as doxycycline hyclate, minocycline, oxytetracycline, chlortetracycline, demechlorcycline, methycycline their pharmaceutical salts and mixtures thereof. In a preferred embodiment of the present invention, the pharmaceutical employed is doxycycline hyclate, an antibiotic with the following structure:

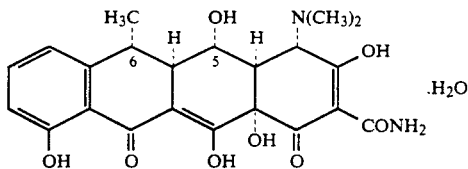

This bacteriostatic compound is effective against a wide variety of gram-negative and gram-positive species and is useful in the treatment of Rocky Mountain Spotted Fever, venereal disease etc. The drug can be incorporated into the delivery system in amounts of from about 20% to about 65% w/w, preferably 55%–60% w/w.

The following examples are provided to more fully describe and delineate that which is considered to be the invention. While it is understood that minor variations and/or alterations in the materials or process parameters may be practiced, it is therefore recognized that said examples are for illustration only and should not be construed as limiting the spirit and scope of the invention as later recited in the claims.

EXAMPLE 1

Doxycycline hyclate cores were prepared by a powder layering technique using the CF Granulator manufactured by Freund—Chemical Ltd, Tokyo, Japan. One (1) kg. of the drug was passed through a Fitzmill NOOO screen. 110 gm. of mannitol and 1 gm. of silicon dioxide ($SiO_2$) were blended together then passed through a U.S. standard mesh no. 100 screen. This blend was then mixed with the milled drug. The final blend was then layered onto 500 gm. of sugar spheres (mesh size 20-25) using hydroxypropylcellulose 8% w/w solution as a binder. The layering granulator conditions were: 1.0 bar atomization; rotor at 160 rpm; a powder delivery rate of 10 rpm; a spray rate of 8 ml./min at 24° C. ml/min; product temp. 24° C. The cores were then dried in an oven at 45° C. overnight.

The active antibiotic cores were coated using a Glatt GPCG3 machine Glatt Air Techniques, Inc., N.J. The coating system employed consisted of Eudragit ® L30D (30% w/w) 41% w/w; triethyl citrate 1.3% w/w; kaolin 2.4% w/w; mannitol 1% w/w; fumaric acid 0.25% w/w water q.s. to 100% w/w. 500 gm. of doxycycline hyclate cores were coated to 6% coating level. The coated pellets were dried in the machine for 45 min at an inlet temp. of 45° C. and product temp. 34° C.

What we claim is:

1. A process for the preparation of a biologically active material as a semi-enteric, sustained release formulation, characterized by a two-tiered solubility profile in the human digestive tract such that initial dissolution begins in the stomach with complete dissolution and absorption of the composition in the intestine, comprising the steps of:
    a) mixing said active with a water soluble bulking agent and a flowability agent,
    b) drying said mixture as a layer or film about an inert core material,
    c) coating said layered core with an aqueous dispersion consisting of a water insoluble methacrylic acid polymer, a water soluble sugar alcohol, a food grade acid and a plasticizer and,
    d) curing said coated active cores so as to effect a substantially hard shell thereon.

2. The process of claim 1 wherein said biologically active material is selected from the group consisting of doxycycline hyclate, minocycline, oxytetracycline, chlortetracycline, demechlorcyline, methacycline and pharmaceutically acceptable mixtures thereof.

3. The process of claim 2 wherein said bulking agent is a sugar alcohol.

4. The process of claim 3 wherein said sugar alcohol is selected from the group consisting of mannitol, sorbitol, lactitol, and mixtures thereof.

5. The process of claim 4 wherein the solubility of said food grade acid is pH dependent.

6. The process of claim 5 wherein said food grade acid is soluble in solutions with a pH of approximately 3.5 and above.

7. The process of claim 6 wherein said food grade acid is selected from the group consisting of fumaric acid, malic acid, citric acid, tartaric acid, ascorbic acid and mixtures thereof.

8. A semi-enteric, sustained release pharmaceutical consisting of a biologically active composition layered on an inert core and an outer inert coating consisting of a water insoluble methacrylic acid polymer, a water soluble sugar alcohol, a food grade acid and a plasticizer characterized by a two-tiered solubility profile in the human digestive tract such that initial dissolution begins in the stomach with complete dissolution and absorption of the composition in the intestine.

* * * * *